(12) United States Patent
Klaue et al.

(10) Patent No.: US 8,672,986 B2
(45) Date of Patent: Mar. 18, 2014

(54) DEVICE FOR TEMPORARILY SPLINTING TOES

(75) Inventors: Kaj Klaue, Savosa (CH); Hans Zwipp, Dresden (DE); Patrick Cronier, Angers (FR); Andrew K. Sands, Amagansett, NY (US)

(73) Assignee: Depuy Synthes Products, LLC, Raynham, MA (US)

( * ) Notice: Subject to any disclaimer, the term of this patent is extended or adjusted under 35 U.S.C. 154(b) by 2617 days.

(21) Appl. No.: 11/245,703

(22) Filed: Oct. 6, 2005

(65) Prior Publication Data

US 2006/0129153 A1 Jun. 15, 2006

Related U.S. Application Data

(63) Continuation of application No. PCT/CH03/00236, filed on Apr. 10, 2003.

(51) Int. Cl.
*A61B 17/86* (2006.01)

(52) U.S. Cl.
USPC .............................................. 606/329; 606/77

(58) Field of Classification Search
USPC .................... 623/21.19, 21.11; 606/300–318
See application file for complete search history.

(56) References Cited

U.S. PATENT DOCUMENTS

| | | | |
|---|---|---|---|
| 4,723,541 A | 2/1988 | Reese | |
| 4,846,162 A * | 7/1989 | Moehring | 606/67 |
| 4,877,019 A * | 10/1989 | Vives | 606/64 |
| 4,915,092 A * | 4/1990 | Firica et al. | 606/67 |
| 4,966,143 A * | 10/1990 | Meinershagen | 606/103 |
| 5,034,012 A * | 7/1991 | Frigg | 606/62 |
| 5,053,035 A * | 10/1991 | McLaren | 606/67 |
| 5,098,435 A * | 3/1992 | Stednitz et al. | 606/916 |
| 5,207,712 A | 5/1993 | Cohen | |
| 5,221,253 A * | 6/1993 | Coll | 604/8 |
| 5,562,665 A * | 10/1996 | Young | 606/62 |
| 5,836,949 A * | 11/1998 | Campbell et al. | 606/62 |
| 5,871,486 A | 2/1999 | Huebner et al. | |
| 5,908,423 A * | 6/1999 | Kashuba et al. | 606/80 |
| 5,919,193 A * | 7/1999 | Slavitt | 606/65 |
| 6,056,749 A | 5/2000 | Kuslich | |
| 6,090,998 A * | 7/2000 | Grooms et al. | 128/898 |
| 6,211,325 B1 * | 4/2001 | Sun et al. | 528/66 |
| 6,402,757 B1 * | 6/2002 | Moore et al. | 606/80 |
| 6,517,541 B1 * | 2/2003 | Sesic | 606/62 |
| 6,524,313 B1 * | 2/2003 | Fassier et al. | 606/63 |
| 6,547,791 B1 * | 4/2003 | Buhren et al. | 606/62 |
| 6,607,530 B1 * | 8/2003 | Carl et al. | 606/914 |
| 7,041,106 B1 * | 5/2006 | Carver et al. | 606/309 |
| 7,799,053 B2 * | 9/2010 | Haid et al. | 606/246 |

(Continued)

FOREIGN PATENT DOCUMENTS

| | | |
|---|---|---|
| EP | 0 682 917 A | 11/1995 |
| FR | 2 809 300 A | 11/2001 |
| GB | 2 355 505 A | 4/2001 |

*Primary Examiner* — Mary Hoffman
(74) *Attorney, Agent, or Firm* — Fay Kaplun & Marcin, LLP

(57) ABSTRACT

A device for temporarily splinting toes, especially for the treatment of hammertoes and other defective positions of toes, consisting of a tube composed of a bio-absorbable material and a guide wire. The tube has an inner diameter of d, whereas the guide wire has an external diameter D, such that D<d. The device enables contact between the ball of the toe and the floor to be reestablished.

13 Claims, 2 Drawing Sheets

(56) References Cited

U.S. PATENT DOCUMENTS

| | | | |
|---|---|---|---|
| 2001/0021871 A1* | 9/2001 | Stinson | 623/1.15 |
| 2003/0158555 A1* | 8/2003 | Sanders et al. | 606/73 |
| 2005/0197660 A1* | 9/2005 | Haid et al. | 606/61 |
| 2007/0156154 A1* | 7/2007 | Schlienger et al. | 606/73 |
| 2007/0182041 A1* | 8/2007 | Rizk et al. | 264/6 |
| 2009/0149890 A1* | 6/2009 | Martin | 606/316 |
| 2009/0210016 A1* | 8/2009 | Champagne | 606/309 |

* cited by examiner

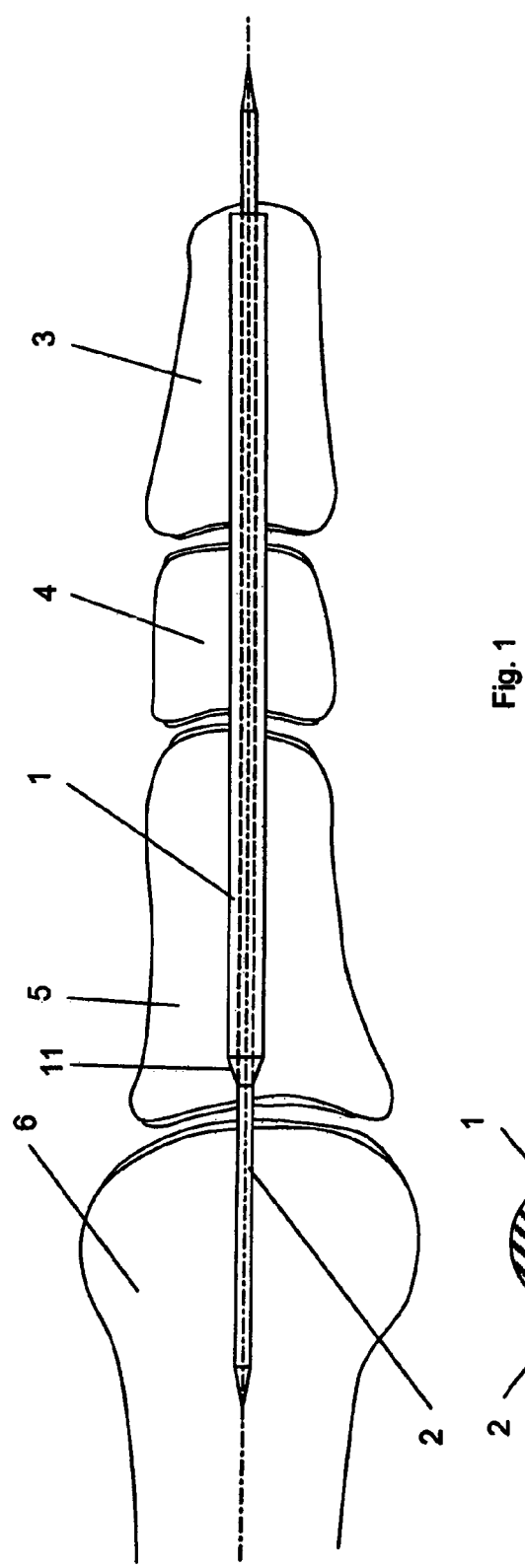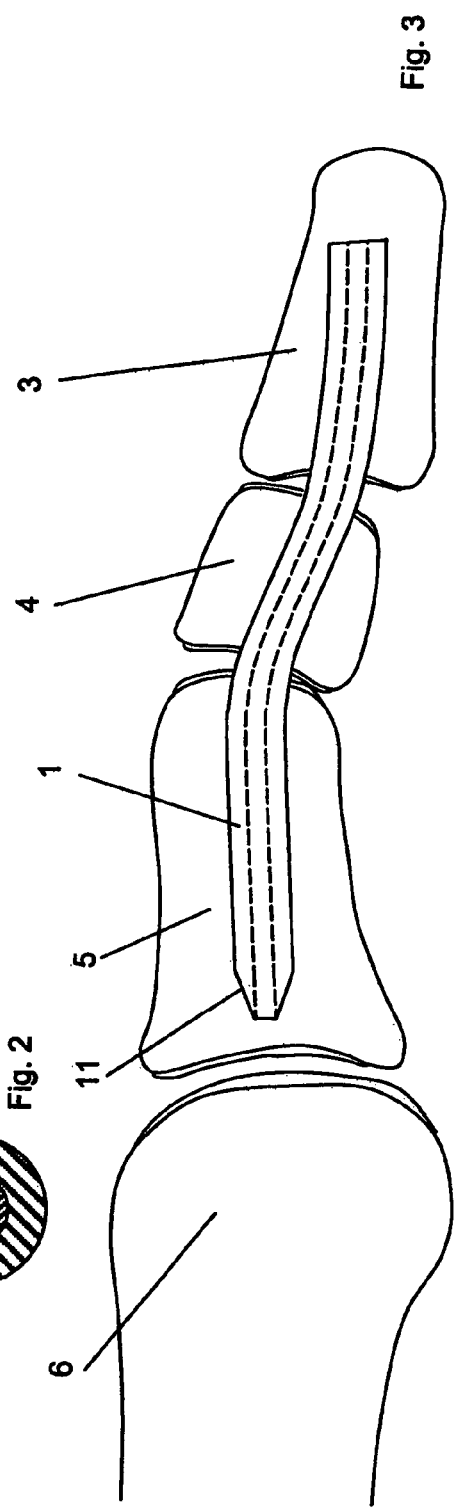

DEVICE FOR TEMPORARILY SPLINTING TOES

CROSS REFERENCE TO RELATED APPLICATION

This application is a continuation of International Patent Application No. PCT/CH2003/000236, filed Apr. 10, 2003, the entire contents of which is expressly incorporated herein by reference.

TECHNICAL FIELD

The present invention relates generally to a device for temporarily splinting toes, especially for treating hammertoes or other defective positions of toes.

BACKGROUND OF THE INVENTION

Treating hammertoes and other defective positions of toes using a Kirschner wire fixation is well known in the state of the art. During the healing period (healing of soft tissue and/or of bones) using a Kirschner wire fixation, a wire protrudes from the tip of the toe. A disadvantage of this known technique is that the patient is almost incapable of working, since he must wear a sort of "bumper bar" (such as a hard rail) to protect the toe and the protruding wire.

The most frequent operation for treating a defective position of a toe is the arthrodesis of the proximal interphalangeal joint, the knitting together of the bones. Frequently, only a joint resection is carried out (the so-called Hohmann operation), whereas a functional operation is also recommended, for which tendons of the end (distal) phalanx are transferred to the proximal phalanx (the so-called Girdlestone and Taylor 1947 operation). Both operations require 6 to 8 weeks of immobilization.

U.S. Pat. No. 5,207,712 (Cohen) discloses an absorbable implant for correcting defective positions of toes. The linear shape of the implant and the lack of cannulation so that the use of a guide wire is not possible are disadvantages of the Cohen implant. A further disadvantage is that it is necessary to remove a substantial amount of bone in order to use the Cohen implant.

SUMMARY OF THE INVENTION

The present invention is to provide a remedy for the above-discussed disadvantages. An object of the present invention is to provide a device, with which it is possible to restore the contact between the ball of the toe and the floor.

The present invention accomplishes this objective with a device comprising a tube composed of a bio-absorbable material and having an internal diameter d, and a guide wire having an external diameter D such that D<d. The outer surface of the tube is smooth.

A surgical procedure for implanting a tube into a toe includes the following steps. Surgical access is achieved over the middle line of the back of the toe. (a) The proximal interphalangeal joint is arthrothomized and the joint surfaces are visualized. (b) The whole of the cartilage is removed and (c) a hole is drilled into the base of the middle phalanx 4 with a 3.5 mm drill. (d) The proximal phalanx 5 is shaped into a point. (e) The toe, slightly shortened thereby, can be straightened from the rigid hammertoe deformation and (f) the proximal phalanx is inserted into the middle phalanx 4 for a trial fit. (g) A metal guide wire 2 is inserted into the 3.5 mm hole axially through the whole of the toe and distally out through the ball of the toe. (h) The drill is then fastened to the distally protruding guide wire 2, whereupon (i) the guide wire 2 is pulled further out, until its other end/tip is barely visible at the base of the middle phalanx 4. (j) The proximal phalanx 5 is definitively plugged into the middle phalanx and held by hand in a proper metatarsophalangeal joint position. (k) The guide wire 2 is then driven with the drill endomedullarly through the properly positioned metatarsophalangeal joint into the metatarsal 6. In rare cases, the guide wire 2 can also be driven only to the base of the proximal phalanx 5. (l) The tube 1 is inserted over the guide 2 wire into the desired position. (m) The tube 1 is cut off at the ball of the toe with special end-cutting nippers. (n) The tube 1 is then driven with a tube ram over the guide wire 2 a few mm under the skin and up to tip of the distal phalanx 3. (o) While manually securing the tube ram, the guide wire 2 is removed distally with the drill. (p) The skin at the tip of the toe is closed with a suture.

Advantages achieved by the use of the present invention include post-operative removal of the implanted bio-absorbable tube may be omitted, the six-week to eight-week "incapacity" of the patient, because of wires protruding from the toes is omitted, and transfixed joints, which are not to be knitted together, can be "arthrolyzed" after six to eight weeks. At the same time, the bio-absorbable tube is selectively broken by the physician.

Other objectives and advantages, in addition to those discussed above, will become apparent to those skilled in the art during the course of the description of the embodiments of the invention which follows. In the description, reference is made to accompanying drawings, which form a part thereof, and which illustrate examples of the invention. Such examples, however, are not exhaustive of the various embodiments of the invention, and therefore, reference is made to the claims that follow the description for determining the scope of the invention.

BRIEF DESCRIPTION OF THE DRAWINGS

FIG. 1 shows a top view of a toe with an endomedullarly introduced guide wire and a bio-absorbable tube, FIG. 2 shows a cross-section of the present invention depicted in FIG. 1, FIG. 3 shows a side view of the toe in FIG. 1 with an endomedullarly introduced bio-absorbable tube after the guide wire has been removed.

DESCRIPTION OF THE PREFERRED EMBODIMENTS

Figure 4:
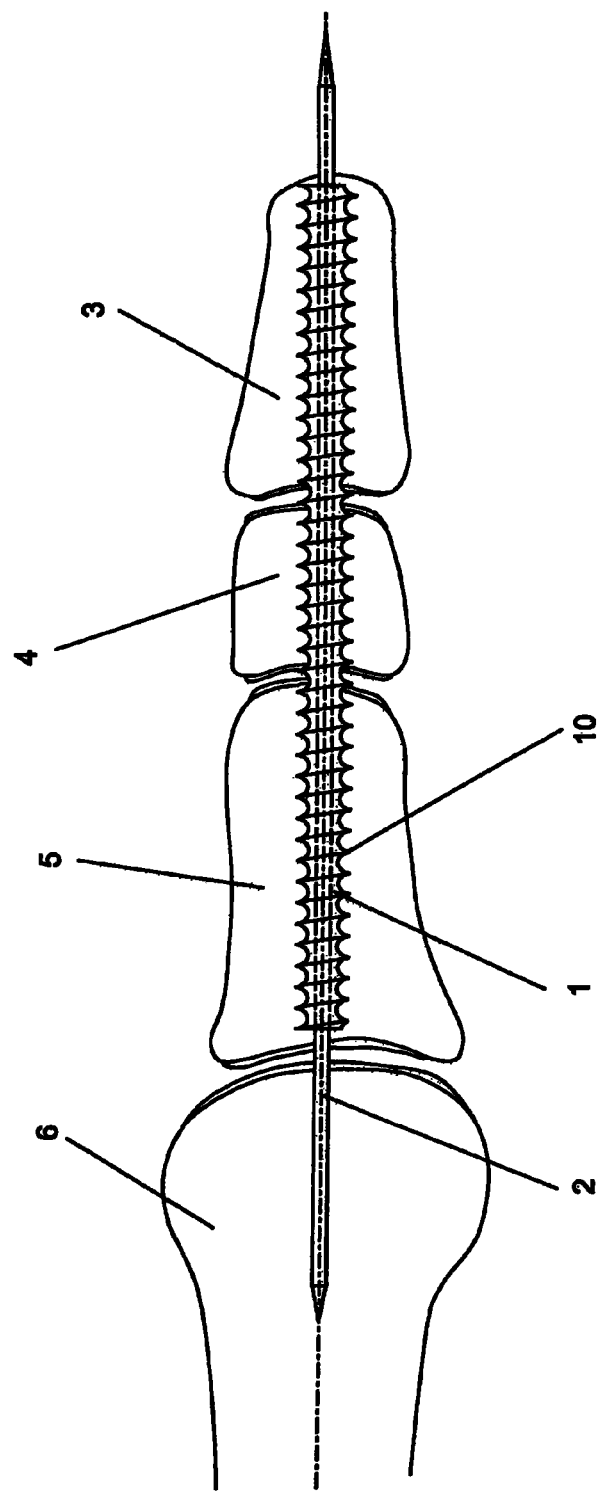
FIG. 4 shows a top view of a toe with an endomedullarly introduced guide wire and a different embodiment of the present invention.

The present invention, shown in FIGS. 1 to 3, is used for temporarily splinting toes, especially for treating hammertoes or other defective positions of toes. The device consists of a tube 1 and a guide wire 2. The tube 1 has an internal diameter "d" and is composed of a bio-absorbable material, such as L-polylactide. The tube 1 may have a length of between 4.5 cm and 5.0 cm, an inside diameter (d) of 1.15 mm, and a wall thickness of 0.25 mm. One end of the tube 1 which is to be inserted into the toe may be tapered such that it forms a point 11. With this tapering, the tube can be implanted more easily.

The outer surface of the tube 1 may be completely smooth. In another embodiment, the outer surface of the tube 1 may consist of an outer thread 10, depicted in FIG. 4. Larger, axially acting forces can be transferred by the bone to the tube 1 by way of the external thread 10.

In a preferred embodiment, the tube 1 may have a bend in one plane. An advantage of this configuration is that during the healing period contact between the ball of the toe and the floor becomes slightly elastic and bending can be accomplished with a slight "tension".

In another embodiment, as depicted in FIG. 3, the tube 1 may be bent in the shape of an "S", so that an anatomically advantageous curvature of the toes which is to be corrected can be achieved.

The bio-absorbable material may have an elongation factor of $\epsilon=(\Delta L \times 100/L) < 10\%$. Better absorbability is an advantage of such a material. Preferably, the length "L" of the implant in situ is approximately 5.0 cm. Either L-polylactide or caprolactone are particularly suitable as bio-absorbable materials. These materials have the advantage that they are absorbed more rapidly by the synovial fluid.

The guide wire 2 may be composed of a metal and have an external diameter "D", where "D" satisfies the condition D<d.

In one embodiment, the guide wire may be linear, so that it can be driven into the tube with the drill.

A brief description of a surgical procedure for implanting a tube 1 into a toe follows in order to explain the invention further.

Surgical access is achieved over the middle line of the back of the toe. (a) The proximal interphalangeal joint is arthrothomized and the joint surfaces are visualized. (b) The whole of the cartilage is removed and (c) a hole is drilled into the base of the middle phalanx 4 with a 3.5 mm drill. (d) The proximal phalanx 5 is shaped into a point. (e) The toe, slightly shortened thereby, can be straightened from the rigid hammertoe deformation and (f) the proximal phalanx is inserted into the middle phalanx 4 for a trial fit. (g) A metal guide wire 2 is inserted into the 3.5 mm hole axially through the whole of the toe and distally out through the ball of the toe. (h) The drill is then fastened to the distally protruding guide wire 2, whereupon (i) the guide wire 2 is pulled further out, until its other end/tip is barely visible at the base of the middle phalanx 4. (j) The proximal phalanx 5 is definitively plugged into the middle phalanx and held by hand in a proper metatarsophalangeal joint position. (k) The guide wire 2 is then driven with the drill endomedullarly through the properly positioned metatarsophalangeal joint into the metatarsal 6. In rare cases, the guide wire 2 can also be driven only to the base of the proximal phalanx 5. (l) The tube 1 is inserted over the guide 2 wire into the desired position. (m) The tube 1 is cut off at the ball of the toe with special end-cutting nippers. (n) The tube 1 is then driven with a tube ram over the guide wire 2 a few mm under the skin and up to tip of the distal phalanx 3. (o) While manually securing the tube ram, the guide wire 2 is removed distally with the drill. (p) The skin at the tip of the toe is closed with a suture.

In an alternative fixation technique, the guide wire 2 and consequently the tube 1 in step (k) of the procedure may be introduced as far as to the metatarsal head. This is particularly advantageous in the event of a metatarsophalangeal instability.

In yet another fixation technique, the guide wire 2 and consequently the tube 1 in step (k) of the procedure is driven up to the base of the proximal phalanx.

The tube 1, six to eight weeks after the implantation, may be broken manually by a physician at the metatarsophalangeal joint in order to restore the flexibility of the toe.

The invention claimed is:

1. A device for temporarily splinting toes, comprising:
a tube sized and shaped to be inserted into a bone of a human toe, the tube composed of a bio-absorbable material having a level of rigidity sufficient to hold portions of the toe in a desired position relative to one another, the tube including an interior channel sized and shaped to receive a guide wire and a bend in a single plane such that, when the tube is inserted into the toe, the bend is contoured to permit contact between the ball of the toe and a floor on which the toe is positioned, an outer diameter of the tube being substantially constant along the bend a guide wire sized and shaped to be slidably received within the interior channel of the tube.

2. A device according to claim 1, wherein the tube is tapered at least at one end.

3. A device according to claim 2, wherein the tapered end ends in a point.

4. A device according to claim 1, wherein the bend is an S-shaped bend.

5. A device according to claim 1, wherein the guide wire is linear.

6. A device according to claim 1, wherein the bio-absorbable material has an elongation factor of $\epsilon=(\Delta L \times 100/L) < 10\%$, where $\Delta L$ is the change in length, and L is the length.

7. A device according to claim 1, wherein the bio-absorbable material is at least one of an L-polylactide or a caprolactone.

8. A device according to claim 1, wherein an internal diameter d of the tube is 1.15 mm.

9. A device according to claim 1, wherein the tube has a wall thickness of 0.25 mm.

10. A device according to claim 1, where the tube has a length between 4.5 cm and 5.0 cm.

11. A device according to claim 1, wherein an outer surface of the tube has an external thread.

12. A device according to claim 1, wherein the guide wire has a point at least at one of its ends.

13. The device according to claim 1, wherein an outer surface of the tube is smooth.

\* \* \* \* \*